US00PP18317P2

(12) United States Plant Patent
Olesen

(10) Patent No.: US PP18,317 P2
(45) Date of Patent: Dec. 18, 2007

(54) ROSE PLANT NAMED 'POULPAL025'

(50) Latin Name: *Rosa hybrida*
Varietal Denomination: Poulpal025

(75) Inventor: Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 25 days.

(21) Appl. No.: 11/447,471

(22) Filed: Jun. 5, 2006

(51) Int. Cl.
*A01H 5/00* (2006.01)

(52) U.S. Cl. ..... Plt./148
(58) Field of Classification Search ..... Plt./148
See application file for complete search history.

*Primary Examiner*—Kent Bell
*Assistant Examiner*—S. B. McCormick-Ewoldt

(57) ABSTRACT

A new garden rose plant of the floribunda class which has abundant, pink flowers and attractive foliage. This new and distinct variety has shown to be uniform and stable in the resulting generations from asexual propagation.

3 Drawing Sheets

Botanical designation: *Rosa* hybrid.
Variety denomination: 'Poulpal025'.

SUMMARY OF THE INVENTION

The present invention constitutes a new and distinct variety of garden rose plant which originated from a controlled crossing between the female seed parent, an unnamed seeding, and the male pollen parent 'Poulelap', described and illustrated in U.S. Plant Pat. No. 10,821.

The two parents were crossed during the summer of 1993 and the resulting seeds were planted in a controlled environment in Fredensborg, Denmark. The new variety, named 'Poulpal025', originated as a single seedling from the stated cross.

The new variety may be distinguished from its female seed parent primarily by flower color. The claimed plant has light pink flowers while the seed parent has deep pink flowers.

The new variety may be distinguished from its male pollen parent by the following combination of characteristics:

1. The pollen parent has orange to yellow orange flower petals while the claimed plant has light pink flower petals.
2. The claimed plant has slightly large flowers than the pollen parent.

The objective of the hybridization of this rose variety was to create a new and distinct variety for garden use with unique qualities, such as:

1. Uniform and abundant pink flowers;
2. Vigorous, but compact growth when propagated both as a budded rose and on its own roots;
3. Exceptional disease resistance; and
4. Improved branching and flower bud development characteristics.

This combination of qualities is not present in previously available commercial cultivars of this type, known to the inventor, and distinguish 'Poulpal025' from all other varieties of which we are aware.

As part of the rose development program, Mogens N. Olesen germinated the seeds from the aforementioned hybridization during winter of 1993 and conducted evaluations on the resulting seedlings in a controlled environment in Fredensborg, Denmark. 'Poulpal025' was selected in the spring of 1994 by the inventor as a single plant from the progeny of the aforementioned hybridization.

Asexual reproduction of 'Poulpal025' by traditional budding and rooted cuttings was first done by Mogens N. Olesen in the nursery in Fredensborg, Denmark in July, 1994. This initial and other subsequent asexual propagations conducted in controlled environments have demonstrated that the characteristics of 'Poulpal025' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'Poulpal025'. Specifically illustrated in the drawings are.

1.

DETAILED DESCRIPTION OF THE VARIETY

Figure 1:
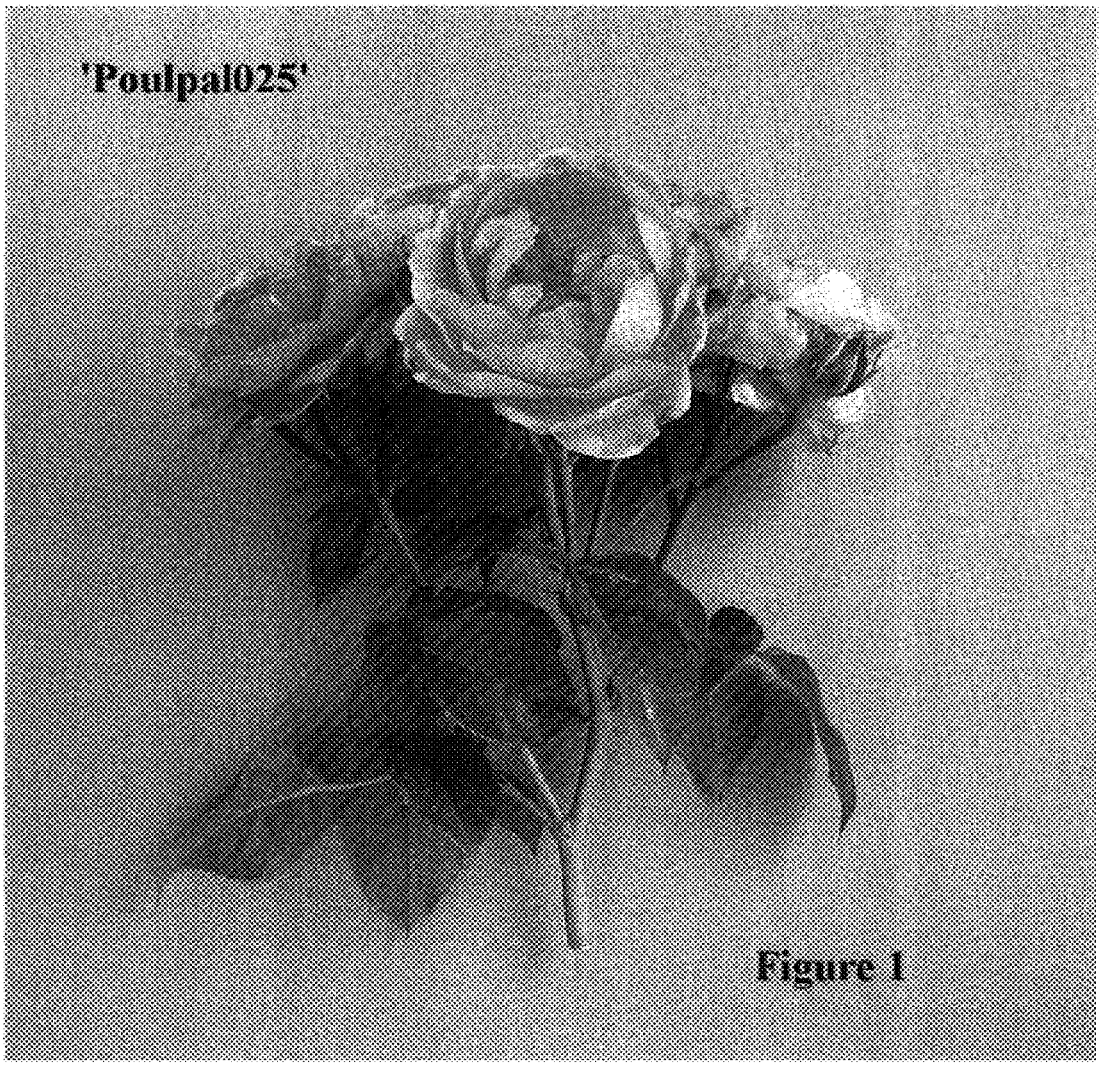
FIG. 1. Cluster of open flowers, peduncles, and pedicels;
2.
Figure 2:
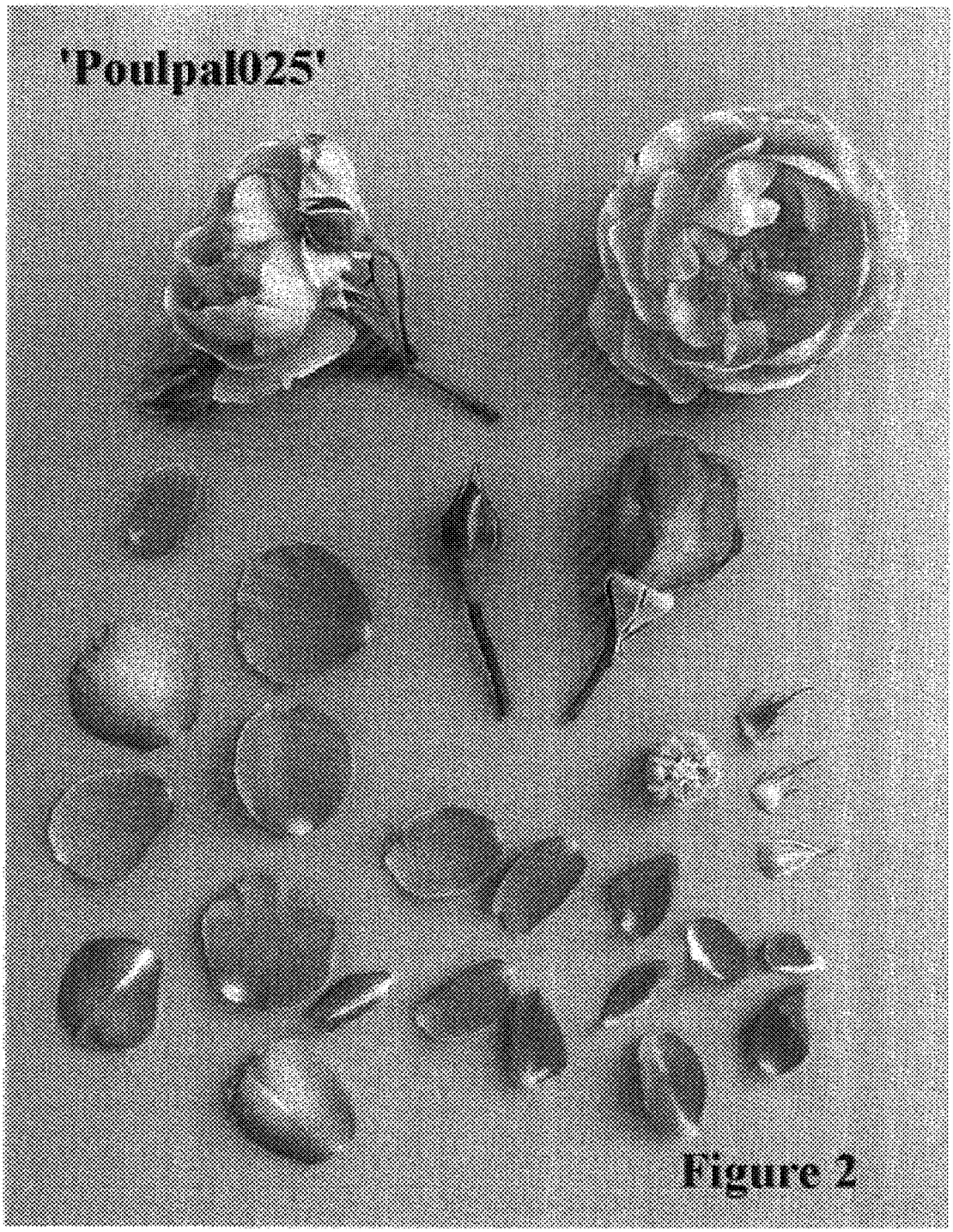
FIG. 2. Various aspects of the flower; and
3.
Figure 3:
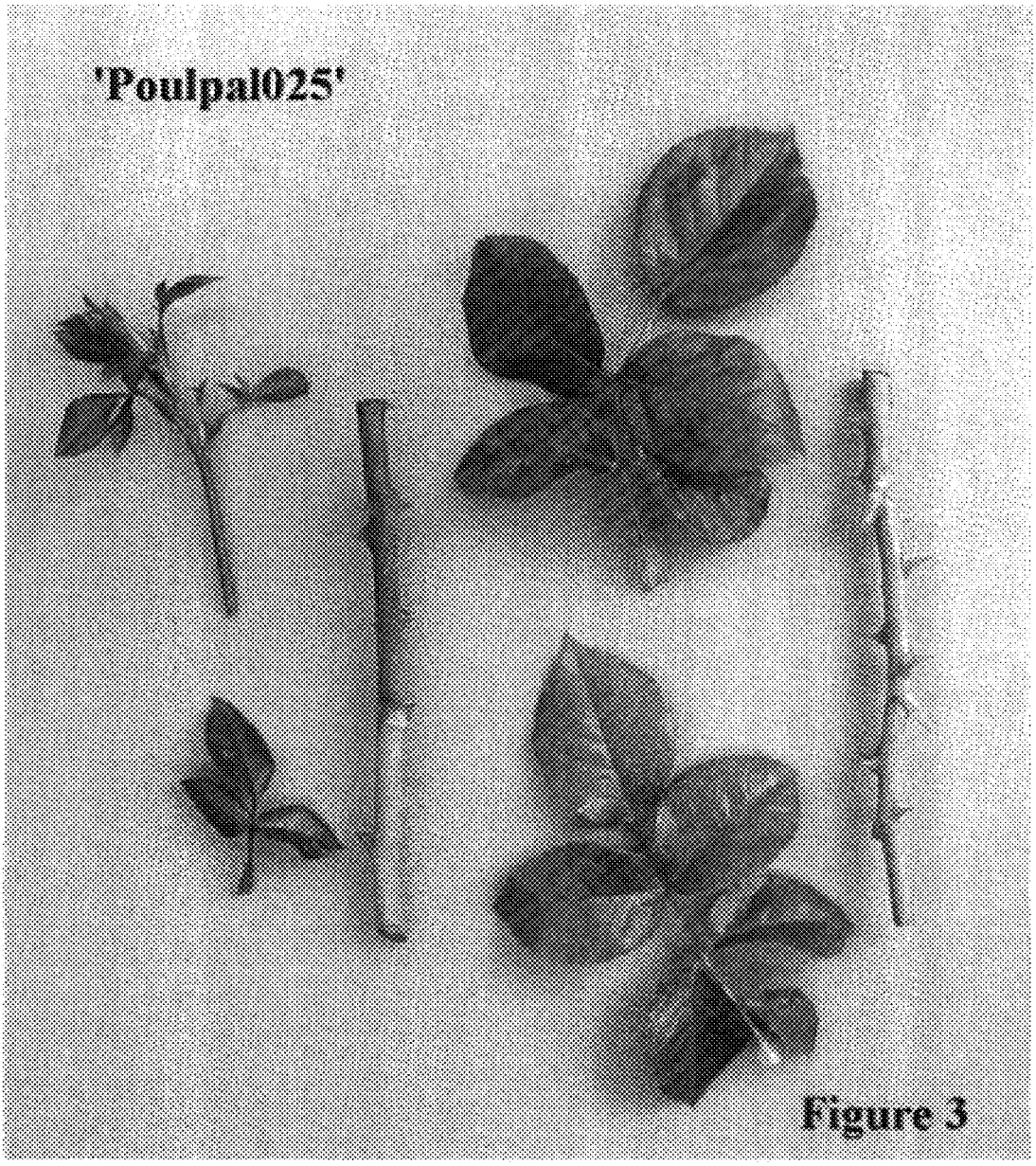
FIG. 3. Various aspects of leaves and stems.

The following is a description of 'Poulpal025', as observed in its growth in in a field nursery in Jackson County, Oreg. Observed plants are 3 years of age, and were grown on *Rosa multiflora* understock. Color references are made using The Royal Horticultural Society (London, England) Colour Chart, 2001, except where common terms of color are used.

For a comparison, several physical characteristics of the rose variety 'Poulmanti', U.S. Plant Pat. No. 11,540, are compared to 'Poulpal025' in Chart 1.

CHART 1

| | 'Poulpal025' | 'Poulmanti' |
|---|---|---|
| Petal Count | 35 total, 15 of which are petaloids | 40 to 50 |

CHART 1-continued

| | 'Poulpal025' | 'Poulmanti' |
|---|---|---|
| Flower Diameter | 75 mm | 60 mm |
| Upon opening upper surface petal color | Red Group 54B | Red Group 55A |

FLOWER AND FLOWER BUD

Blooming habit: Recurrent.

Flower bud:

*Size.*—Upon opening, 30 mm average length from base of receptacle to end of bud. Bud diameter is normally 15 mm.

*Bud form.*—Pointed ovoid.

*Bud color.*—As sepals unfold, petals are Red Group 45B with intonations of Orange-Red Group N34A.

*Sepal inner surface.*—Color: Yellow-Green Group 147C with anthocyanic intonations the color of Greyed-Red Group 181A. Surface: Strong pubescence observed.

*Sepal outer surface.*—Color: Yellow-Green Group 146B with anthocyanic intonations the color of Greyed-Orange Group 176A. Texture: Rough with many stipitate glands.

*Sepal shape.*—Apex: Cirrhose. Base: Flat at union with receptacle.

*Sepal margin.*—Margins have medium foliaceous appendages on three of the five sepals.

*Sepal size.*—20 mm long by 10 mm wide.

*Receptacle.*—Texture: Smooth. Shape: Elongate funnel shaped. Size: 13 mm in length by 8 mm wide. Color: Yellow-Green Group 144A. Anthocyanic pigments the color of Greyed-Orange Group 173A observed.

*Peduncle.*—Length: 9 cm on average. Diameter: 3 to 4 mm. Surface Texture: Smooth. Color: Yellow-Green Group 146C. Anthocyanic intonations the color of Greyed-Orange Group 166B observed.

*Pedicel.*—Surface: Rough. Length: 30 to 35 mm. Diameter: 2.5 mm on average. Color: Yellow-Green Group 144B with strong anthocyanic pigments the color of Greyed-Red Group 178B observed. Strength: Moderate to strong.

Flower bud development: Flower buds are borne in clusters of 3 to 5 flower buds per stem. Flower arrangement is most similar to a corymb.

Flower bloom:

*Fragrance.*—Light floral.

*Duration.*—The blooms have a duration on the plant of approximately 7 to 10 days. Petals fall cleanly away from plant after flowers have fully matured.

*Size.*—Flower diameter is 75 mm on average when open. Flower depth is 25 mm.

*Flower shape.*—General shape is a semi-double flower which is fully open and calathiform. All flower reproductive parts are unobstructed when flowers are fully mature. Shape of flower, side view: Upon opening the upper portion is flat. The lower portion is convex. After opening, the upper portion is flat. The lower portion is convex.

*Petalage.*—Under normal conditions, flowers have 35 petals total, 15 of which are petaloids.

*Petal color.*—Upon opening, outer petals Upper surface: Red Group 54B. Lower surface: Red-Purple Group 58B with intonations of 58C. Upon opening, inner petals: Upper surface: Red Group 52A with intonations of 52B. Lower surface: Red-Purple Group 58B with intonations of Red-Purple Group 58D. Light overlay of Red-Purple Group 58D at the mid section running vertically. Basal petal spots, upon opening: Upper surface: Yellow Group 3C. Lower surface: Yellow Group 4D. After opening, outer and inner petals: Upper surface: Red Group 48C at basal petal zone. Middle and marginal zones are Red Group 55B. Lower surface: Basal zone is Red Group 51B. Middle and marginal zones there is an overlay of Red Group 55C. At the margins Red-Purple Group 58B. Basal petal spots, after opening: Upper surface: Yellow Group 3C. Lower surface: Yellow Group 4D. Variations in color: Upper and lower petals surfaces occasionally exhibit vertical streaks the color of Red Group 56C.

General tonality: On open flower Red-Purple Group N57D with intonations of Red-Purple Group 58C. After flowers have matured, general tonality becomes Red-Purple Group 62A to 62B with intonations of Red-Purple Group 61D.

Petals:

*Petal reflex.*—None.

*Margin.*—Entire and uniform.

*Shape.*—Generally broadly elliptical in shape. Apex shape: Round. Base shape: Acute.

*Size.*—27 to 42 mm (l)×23 to 38 mm (w).

*Texture.*—Smooth.

*Thickness.*—Average to somewhat thin.

Petaloids:

*Quantity.*—15 on average.

*Shape.*—Irregular, asymmetrical. The base is very acute. The apex is round to acute. Occasionally, petaloids have a cleft at the center of the margin.

*Color.*—As observed in flower petals after opening.

*Size.*—On average, 32 mm in length by 20 mm wide.

Reproductive organs:

*Pollen.*—None observed.

*Anthers.*—Size: Normally 2.5 mm in length. Color: Greyed-Orange Group 163A. Quantity: 155 on average.

*Filaments.*—Color: Yellow Group 11B. Length: On average 10 mm.

*Pistils.*—Length: Normally, 4 mm. Quantity: On average 50.

*Stigmas.*—Inferior in location relative to the length of the filaments and the height of the anthers. Color: Yellow Group 4D.

*Styles.*—Color: Yellow Group 11D.

*Hips.*—None Observed in the field nursery in Jackson County Oreg.

PLANT

Plant growth: Moderate, upright to bushy. When grown as a budded field grown plant on *Rosa multiflora* understock, the height of the plant is from 40 to 60 cm. The average width is 50 cm.

Stems:

*Color.*—Juvenile growth: Yellow-Green Group 145A with intense anthocyanic intonations Greyed-Orange Group 176B with intonations of Greyed-Orange Group 175A. Mature growth: Yellow-Green Group 144B with intonations of Yellow-Green Group 146C.

*Diameter.*—On average, 10 mm.

*Internodes.*—On mature canes, there is an average distance of 30 to 50 mm between nodes.

*Surface texture.*—Young wood: Smooth. Older wood: Smooth.

Prickles:

*Incidence.*—8 to 9 prickles per 10 cm of stem.

*Size.*—Average length of prickles on mature stems is 9 mm.

*Shape.*—Upper and lower portions are concave.

*Color.*—Juvenile prickles: Greyed-Red Group 181B. Mature prickles: Greyed-Orange Group N170B.

Plant foliage: Normal number of leaflets leaves in middle of the stem: 5 leaflets.

*Compound leaf.*—135 to 145 mm (l)×100 to 120 mm (w).

*Quantity.*—3 leaves per 10 cm of stem on average.

*Color of mature foliage.*—Upper side: Yellow-Green Group 146A with intonations of Yellow-Green Group 147A. Lower side: Yellow-Green Group 147C.

*Color of juvenile foliage.*—Upper side: Yellow-Green Group 144A with predominant anthocyanic intonations the color of Greyed-Orange Group 166A. Lower side: Yellow-Green Group 144A with intonations of Yellow-Green Group 144B with predominant anthocyanic intonations the color of Greyed-Orange Group 166A.

Plant leaves and leaflets:

*Stipules.*—Size: Normally 22 mm in length. Quantity: 2 per compound leaf. Shape: Linear, slightly broad based with outward extending apecies. Margins: Finely serrated with many stipitate glands. Color: Yellow-Green Group 146B.

*Petiole.*—Length: 30 to 35 mm. Diameter: 2 mm on average.

*Upper surface.*—Color: Yellow-Green Group 146C.

*Lower surface.*—Color: Yellow-Green Group 144B. Observations: Few prickles observed.

*Rachis.*—Length: 50 mm on average.

*Upper surface.*—Color: Yellow-Green Group 146C. At the point of leaflet attachment anthocyanic intonations the color of Greyed-Red Group 182A observed.

*Lower surface.*—Color: Yellow-Green Group 144B. Observations: Prickles observed.

*Leaflet.*—Edge: Serrated. Size: Average size of the terminal leaflet on normal leaves is 60 to 65 mm in length by 40 to 45 mm wide. Shape: Generally broadly elliptical. Base: Obtuse. Apex: Cuspidate. Thickness: Average to thick. Texture: Smooth. Arrangement: Odd pinnate. Venation: Reticulate. Glossiness: Moderately glossy.

*Disease resistance.*—Above average resistance to powdery and downy mildew, rust, black spot, and *Botrytis* under normal growing conditions in Jackson County, Oreg.

*Cold hardiness.*—The variety is tolerant to USDA Cold Hardiness Zone 6.

*Heat tolerance.*—The variety has been found to be suitable for climate conditions found in the American Horticulture Society heat zone 7.

What is claimed is:

1. A new and distinct variety of rose plant of the floribunda rose class named 'Poulpal025', substantially as illustrated and described herein, due to its abundant pink flowers, disease resistance, and extended period of bloom.

* * * * *